US010631975B2

(12) United States Patent
Govari et al.

(10) Patent No.: US 10,631,975 B2
(45) Date of Patent: Apr. 28, 2020

(54) DETECTION OF LEAKAGE IN IMPLANTS

(71) Applicant: Biosense Webster (Israel) Ltd., Yokneam (IL)

(72) Inventors: Assaf Govari, Haifa (IL); Christopher Thomas Beeckler, Brea, CA (US); Yehuda Algawi, Binyamina (IL); Yaron Ephrath, Karkur (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 338 days.

(21) Appl. No.: 15/274,107

(22) Filed: Sep. 23, 2016

(65) Prior Publication Data
US 2018/0085210 A1 Mar. 29, 2018

(51) Int. Cl.
*A61F 2/12* (2006.01)
*A61B 5/053* (2006.01)
(Continued)

(52) U.S. Cl.
CPC ............. *A61F 2/12* (2013.01); *A61B 5/0538* (2013.01); *G01M 3/187* (2013.01); *A61B 5/686* (2013.01); *A61B 5/6867* (2013.01); *A61F 2210/0076* (2013.01); *A61F 2230/0071* (2013.01); *A61F 2240/002* (2013.01); *A61F 2250/0003* (2013.01); *A61F 2250/008* (2013.01)

(58) Field of Classification Search
CPC ................ A61F 2/12; A61F 2250/0003; A61F 2240/002; A61F 2210/0076; A61F 2230/0071; A61F 2250/008; G01M 3/187; A61B 5/0538; A61B 5/686; A61B 5/6867; A61B 2250/008
See application file for complete search history.

(56) References Cited

U.S. PATENT DOCUMENTS

2006/0111632 A1 5/2006 Chen
2009/0012372 A1* 1/2009 Burnett ................. A61B 5/076
                                                    600/300
(Continued)

FOREIGN PATENT DOCUMENTS

WO   WO 2006/135857 A2   12/2006

OTHER PUBLICATIONS

EP17192739.5—1115—Extended European Search Report dated Jan. 30, 2018.

*Primary Examiner* — Dinah Baria
*Assistant Examiner* — Rokhaya Diop
(74) *Attorney, Agent, or Firm* — Eugene L. Szczecina, Jr.

(57) ABSTRACT

An implant includes a hollow biocompatible shell, first and second electrodes, filling material, and circuitry. The hollow biocompatible shell is configured to be implanted in an organ of a patient. The first electrode is disposed inside the shell. The second electrode has at least one surface disposed outside the shell. The filling material, which includes carbon nanotubes (CNT), fills the shell and is configured, in response to a rupture occurring in the shell, to change a spatial orientation of the CNT and thus to cause a change in electrical conductivity of the filling material between the first electrode and the rupture. The circuitry is electrically connected to the first and second electrodes and is configured to detect the rupture by sensing the change in the electrical conductivity of the CNT, and to produce an output indicative of the detected rupture.

14 Claims, 3 Drawing Sheets

(51) Int. Cl.
 *G01M 3/18* (2006.01)
 *A61B 5/00* (2006.01)

(56) References Cited

U.S. PATENT DOCUMENTS

2010/0308279 A1   12/2010   Zhou et al.
2011/0137413 A1   6/2011   Osypka
2013/0018112 A1   1/2013   Thielemans et al.
2014/0199915 A1   7/2014   Pham et al.
2016/0229983 A1*  8/2016   Ikeno .................... C08L 83/04

* cited by examiner

DETECTION OF LEAKAGE IN IMPLANTS

FIELD OF THE INVENTION

The present invention relates generally to cosmetic implants, and particularly to methods and systems for detecting leakage in medical implants.

BACKGROUND OF THE INVENTION

Various types of implants, such as breast implants, are used in a variety of therapeutic and cosmetic applications.

For example, U.S. Patent Application Publication 2009/0012372, whose disclosure is incorporated herein by reference, describes a method for sensing rupture of an implant (such as a breast implant) that has been implanted in body tissues or in an organ of a patient. In one embodiment, a system includes a sensor coupled to an outer surface of the implant and configured to measure a property at the outer surface of the implant, for example, electrical conduction, chemical composition, or an optical property that is indicative of whether an implant rupture has occurred. The sensor is also configured to transmit a wireless signal to a device external to the body, which alerts the patient or a healthcare provider whether the measured property indicates that the implant rupture may have occurred.

U.S. Patent Application Publication 2006/0111632, whose disclosure is incorporated herein by reference, describes methods and systems for detecting wall breach in inflatable prostheses rely on intrusion of a body fluid or inflation medium to electrically alter a signaling circuit. In one embodiment, an open portion of a circuit is closed to enable or modify a transmitted signal. In another embodiment, electrical current is generated to power an electrical transmission.

PCT Patent Application WO 2006/135857, whose disclosure is incorporated herein by reference, describes a device and method that communicate, to a patient and/or healthcare professionals, the failure, rupture, or breakage of a barrier within an implant. The device consists of an implantable sensor and an alerting mechanism. The device may include an internal power source and may employ software to allow for external programming and/or interrogation of the device. The device may also be recharged and/or powered through an external source.

SUMMARY OF THE INVENTION

An embodiment of the present invention that is described herein provides an implant including a hollow biocompatible shell, first and second electrodes, filling material, and circuitry. The hollow biocompatible shell is configured to be implanted in an organ of a patient. The first electrode is disposed inside the shell. The second electrode has at least one surface disposed outside the shell. The filling material, which includes carbon nanotubes (CNT), fills the shell and is configured, in response to a rupture occurring in the shell, to change a spatial orientation of the CNT and thus to cause a change in electrical conductivity of the filling material between the first electrode and the rupture. The circuitry is electrically connected to the first and second electrodes and is configured to detect the rupture by sensing the change in the electrical conductivity of the CNT, and to produce an output indicative of the detected rupture.

In some embodiments, the filling material includes silicone gel in which the CNT are doped. In other embodiments, the second electrode is electrically insulated from the filling material and electrically connected to a tissue of the organ surrounding the shell. In yet other embodiments, the circuitry is configured to issue an alert indicative of the rupture to a device external to the patient body.

In an embodiment, the circuitry is configured to wirelessly receive electrical power from a device external to the patient body. In another embodiment, the implant further includes a power source having first and second terminals that are electrically connected to the first and second electrodes, respectively. In response to the rupture, the power source is configured to drive electrical current via the first and second electrodes and via tissue of the organ surrounding the shell. In yet other embodiments, the power source is disposed inside the shell.

In some embodiments, the circuitry is configured to charge the power source wirelessly from a device external to the patient body. In other embodiments, the power source is configured to supply power to the circuitry. In yet other embodiments, the shell is configured to electrically insulate the filling material from the organ. In an embodiment, the circuitry is configured to generate an internal operating power wirelessly from a field induced by a device external to the patient body.

There is additionally provided, in accordance with an embodiment of the present invention, a method for producing an implant including providing a hollow biocompatible shell to be implanted in an organ of a patient. A first electrode is disposed inside the shell. A second electrode is coupled to the shell, wherein at least one surface of the second electrode is disposed outside the shell. Circuitry is disposed inside the shell and electrically connecting the circuitry to the first and second electrodes. The shell is filled with a filling material including carbon nanotubes (CNT) and is sealed.

There is additionally provided, in accordance with an embodiment of the present invention, a method including operating circuitry in an implant that is implanted in an organ of a patient. The implant includes a hollow biocompatible shell, and filling material, which includes carbon nanotubes (CNT). The filling material fills the shell and, in response to a rupture occurring in the shell, changes a spatial orientation of the CNT and thus causes a change in electrical conductivity of the filling material between a first electrode disposed inside the shell and the rupture. The circuitry is electrically connected to the first electrode, and to a second electrode having at least one surface disposed outside the shell. A rupture caused to the shell is detected, using the circuitry, by sensing the change in the electrical conductivity of the CNT, and an output indicative of the detected rupture is produced.

There is further provided, in accordance with an embodiment of the present invention, a system including an implant and an external device. The implant includes a hollow biocompatible shell, first and second electrodes, filling material, and circuitry. The hollow biocompatible shell is configured to be implanted in an organ of a patient. The first electrode is disposed inside the shell. The second electrode having at least one surface is disposed outside the shell. The filling material, which includes carbon nanotubes (CNT), fills the shell and is configured, in response to a rupture occurring in the shell, to change a spatial orientation of the CNT and thus to cause a change in electrical conductivity of the filling material between the first electrode and the rupture. The circuitry is electrically connected to the first and second electrodes, and is configured to detect the rupture by sensing the change in the electrical conductivity of the CNT, and to produce an output indicative of the detected rupture. The external device is configured to receive the output from the implant and to issue an alert indicative of the detected rupture.

The present invention will be more fully understood from the following detailed description of the embodiments thereof, taken together with the drawings in which:

DETAILED DESCRIPTION OF EMBODIMENTS

Overview

Figure 1:
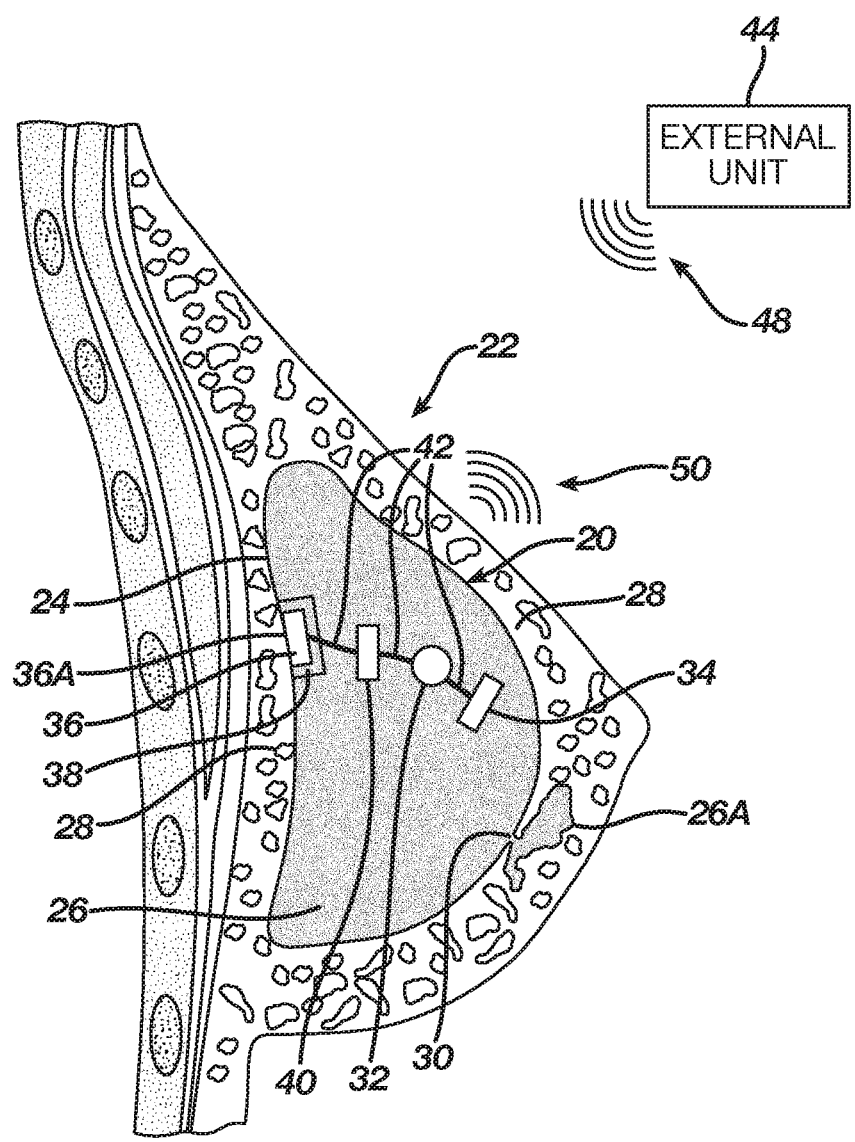
FIG. 1 is a schematic, pictorial illustration of a system for detecting leakage in a breast implant, in accordance with embodiments of the present invention.

Breast implants, are typically used for reconstructing a human breast after excision or for shaping the size and contour of breasts in cosmetic applications. A breast implant typically comprises a filling material, also known as implantable material, such as silicone gel that conforms to the texture of natural tissue of the breast. The implant further comprises a biocompatible shell adapted to encapsulate the implantable material and to be implanted in the human breast so as to resemble the texture of the breast tissue. The shell typically comprises a soft and flexible material that has no physical or chemical interactions with the surrounding tissue. Although breast implants are designed to last many years, they are still vulnerable to physical damage and have limited durability against punctures.

Leakage of the silicone gel, due to some sort of puncture or break in the outer shell is typically invisible and is unfelt by the patient having the implant. Such leakage may cause serious medical problems, especially when the gel is in contact with the breast tissue for a long period of time. To avoid such problems, a patient having a breast implant conventionally has to undergo periodical check-ups to detect any leakage of the gel. For example, the federal drug and administration (FDA) recommends performing a magnetic resonance imaging (MRI) scan 3 years after an implant procedure, and then to repeat the scan every second year, so as to detect possible rupture.

Embodiments of the present invention that are described herein provide techniques for detecting leakage from implants. In the disclosed embodiments, an implant comprises a hollow shell filled with filling material, typically a silicone gel. In some embodiments, the gel comprises carbon nanotubes (CNT) that affect its electrical conductivity. When the implant is functional, the CNT are randomly oriented and the conductivity has a certain baseline value. If the implant ruptures and filling material leaks, the CNT align so that their longitudinal axes become oriented in parallel with the direction of the leakage. As a result, the electrical conductivity of the filling material in the vicinity of the rupture improves (increases) considerably relative to the baseline value.

In some embodiments, the leakage is detected by sensing the change in the electrical conductivity of the filling material caused by re-orientation of the CNT. In an embodiment, the implant comprises a first electrode disposed inside the shell, and a second electrode having at least one surface outside the shell. The first electrode is in electrical contact with the filling material. The second electrode is electrically insulated from the filling material, and is in electrical contact with the tissue surrounding the implant. The implant further comprises circuitry that detects a rupture by sensing a change in electrical conductivity between the two electrodes.

In an event of a rupture, some of the gel leaks through the rupture and physically contacts the breast tissue. The carbon nanotubes align toward the rupture and such that the electrical conductivity of the gel between the first electrode and the rupture increases. An electrically-conductive path thus forms from the first electrode, via the filling material, the rupture, the surrounding tissue, to the second electrode. The circuitry is therefore able to detect the rupture by sensing an increase in electrical conductivity between the two electrodes. Upon detecting a rupture, the circuitry may issue an alert or other indication to an external device so that the patient is alerted. The disclosed techniques improve patient safety by providing early detection of the ruptures and leakage. In addition, these techniques reduce the need for periodical MRI check, thus reducing cost and radiation exposure.

System Description

FIG. 1 is a schematic pictorial illustration of a breast implant 20 implanted in a women's breast 22, in accordance with an embodiment of the present invention. Typically, implant 20 is a prosthesis used to shape the size and contour of breast 22.

Breast 22 comprises natural tissue 28 surrounding implant 20. Implant 20 comprises a shell 24 encapsulating gel 26, which is a soft filling material that resembles the texture of tissue 28. In some embodiments, shell 24 creates physical as well as electrical insulation between gel 24 and tissue 28. The gel is adapted to shape the size and contour of breast 22. Gel 26 may comprise an electrically insulating silicone gel, or any other suitable filling material. In some embodiments, gel 26 is doped with carbon nanotubes (CNT) that increase the electrical conductivity of the gel depending on their concentration and spatial orientation as will be described in detail in FIG. 2.

In the example of FIG. 1, implant 20 is ruptured at the lower right area. A rupture 30 in shell 24 causes leakage of some amount of gel 26A from implant 20 into tissue 28. Gel 26A is substantially identical in composition to gel 26 and denoted 26A to mark the portion of gel 26 that has leaked out of the implant into tissue 28. Gel 26A that has leaked out is in direct contact with tissue 28.

In some embodiments, implant 20 comprises an internal electrode 34 disposed inside shell 24. A layer 38 made of a biocompatible electrical insulator, such as silicone, glass, ceramic, or liquid crystal polymer (LCP), is disposed between gel 26 and a second electrode 36 so as to prevent physical contact between gel 26 and electrode 36. A surface 36A of electrode 36 is in physical contact with tissue 28 so that electrode 36 is electrically connected to tissue 28 but electrically insulated from gel 26.

Implant 20 further comprises a power source, such as a battery 32 having two terminals. Wires 42 connect one terminal (e.g., positive) of battery 32 to electrode 34 and the other (e.g., negative) terminal to electrode 36. Wires 42 are configured to electrically conduct current between the battery and the electrodes, but are electrically insulated from gel 26.

Electrical circuitry 40, is disposed between, and connected, via wires 42, to battery 32 and electrode 36, and configured to sense the level of electrical current flowing between electrodes 34 and 36 via the battery. In some embodiments, circuitry 40 is configured to wirelessly send radio-frequency (RF) signals 50 indicating the sensed current level, to an external unit 44.

In some embodiments, external unit 44 may be a handheld device capable of receiving and decoding RF signals (e.g., a dedicated device or a mobile phone having a suitable application) used by the patient that was implanted with implant 20 or by a physician (not shown). In some embodiments, in addition to receiving RF signals 50, unit 44 also transmits RF signals 48, e.g., to wirelessly power circuitry 40. Unit 44 is further configured to provide the patient with an alert when rupture is detected. The rupture detection mechanism is depicted and described in detail in FIG. 2 below.

In alternative embodiments, circuitry 40 is configured to charge battery 32 using RF signals 48 received wirelessly from unit 44 so that the battery may power circuitry 40 via wires 42.

The configuration of implant 20 shown in FIG. 1 is an example configuration that is shown purely for the sake of conceptual clarity. In alternative embodiments, any other suitable configuration can be used. For example, any other suitable power source, such as an alternating current (AC) voltage source may be used instead of battery 32 in FIG. 1 above.

Figure 2:
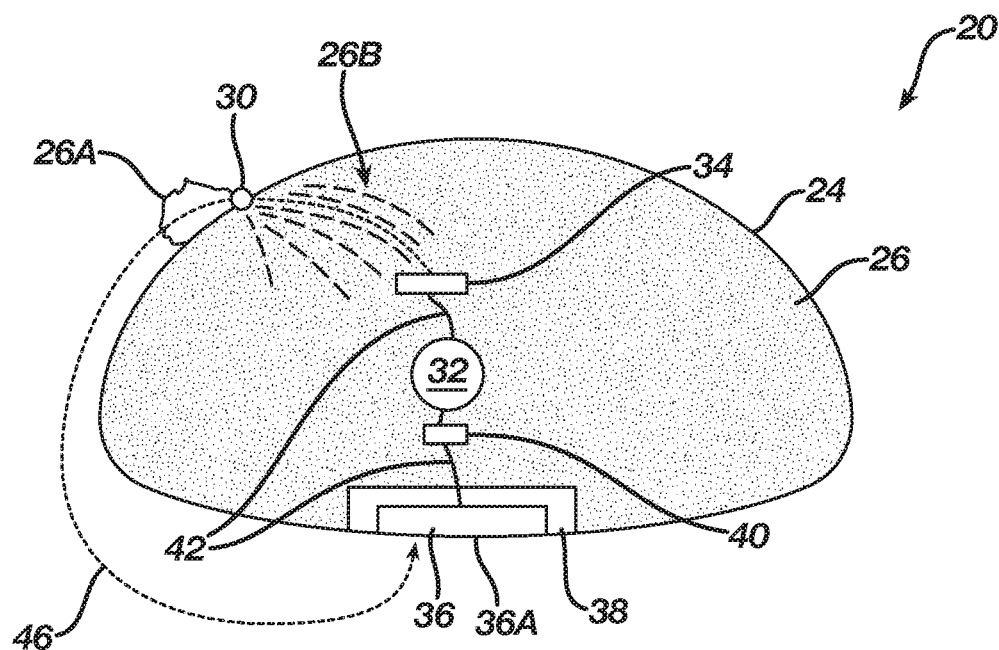
FIG. 2 is a schematic, pictorial illustration of a breast implant, in accordance with embodiments of the present invention.

FIG. 2 is a schematic, pictorial illustration of punctured breast implant 20, in accordance with an embodiment of the present invention. Rupture 30 causes leakage of gel 26A from implant 20 into tissue 28. As shown in an area 26B, the carbon nanotubes align longitudinally in the rupture, thus increasing the electrical conductivity of gel 26 between electrode 34 and rupture 30. The electrical current flows from the positive terminal of battery 32 to electrode 34, and exiting implant 20 through rupture 30. The current further flows externally to implant 20 as shown by an arrow 44, via gel 26A and tissue 28, into electrode 36. The current enters implant 20 via wire 42 and circuitry 40, to close the electrical circuit to the negative terminal of battery 32. Circuitry 40 measures the level of electrical current between electrode 36 and battery 32 and issues an alert upon detecting a significant change in the electrical conductivity.

In some embodiments, circuitry 40 wirelessly transmits an indication of the change in the electrical conductivity to external unit 44, using RF signals 50, as shown in FIG. 1.

In other embodiments, circuitry 40 periodically reports the current level to external unit 44, which decides when a significant change in the electrical current level has occurred, indicating of a rupture.

Figure 3:
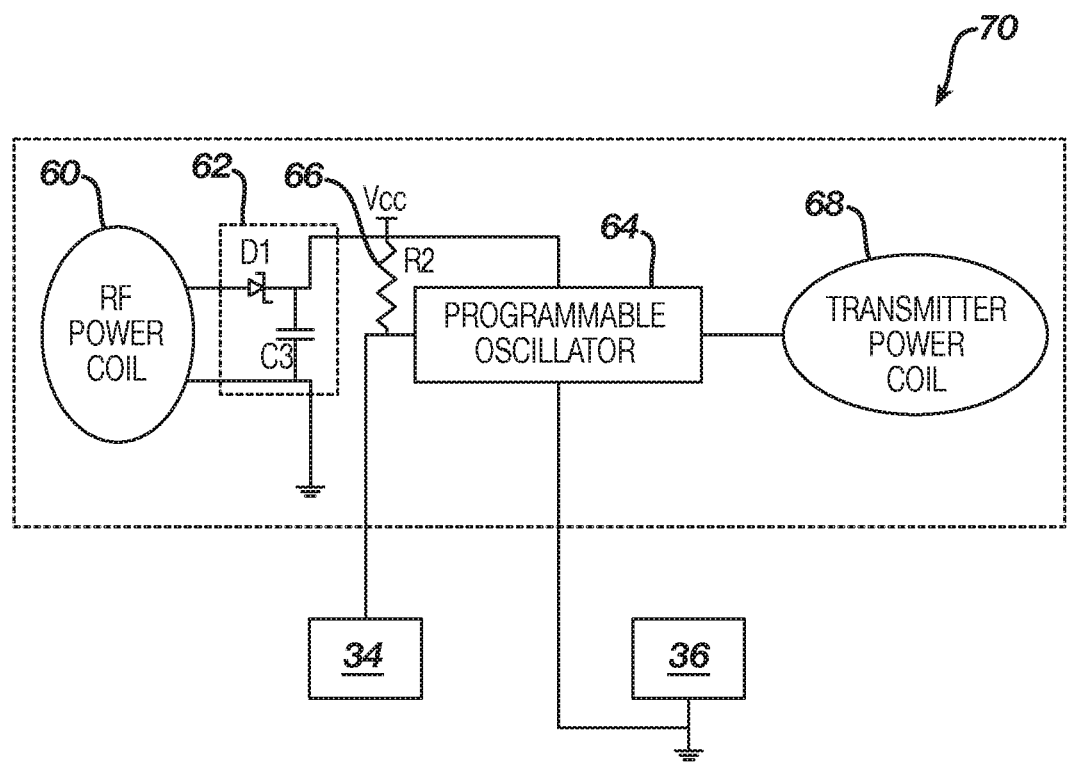
FIG. 3 is a block diagram that schematically illustrates leakage detector circuitry, in accordance with an embodiment of the present invention.

FIG. 3 is a block diagram that schematically illustrates leakage detector circuitry 70, in accordance with an embodiment of the present invention. Circuitry 70 may replace, for example, battery 32 and circuitry 40 of FIG. 1 above. In this embodiment, there is no battery in implant 20. Instead, circuitry 70 is configured to receive RF signals 48 from external unit 44, and to generate internal operating power from signals 48. The operating power is used by circuitry 70 for sensing the current level in implant 20, and for wirelessly sending RF signals 50 that indicate the sensed current level to external unit 44.

In some embodiments, circuitry 70 comprises an RF power coil 60, which is configured to receive signals 48 transmitted from unit 44. Circuitry 70 further comprises a rectifier 62, which is configured to rectify the electrical voltage inducted across coil 60 by signals 48. Rectifier 62 in the present example comprises a diode D1 and a capacitor C3. In this example the capacitance of C3 is 4.7 nanoFarad (nF), but any other suitable capacitance can be used. The rectified voltage is used for charging capacitor C3 up to a voltage level of VCC volts (e.g., 3V-5V), used for operating circuitry 70.

Circuitry 70 comprises a programmable oscillator 64, which is configured to produce a signal whose frequency depends on an input control voltage provided to the oscillator. In the circuitry of FIG. 3, this input control voltage depends on a ratio between a constant resistance (e.g., 100 K Ohm) of a resistor 66 denoted R2, and the variable resistance between electrodes 34 and 36 indicating the sensed current level. Thus, oscillator 64 generates an output signal whose frequency is indicative of the current level between electrodes 34 and 36.

Circuitry 70 further comprises a transmitter power coil 68, which is configured to transmit RF signals 50 for indicating the sensed current level to unit 44. In alternative embodiments, the frequency of signals 50 may belong to a frequency range lower than an RF range, such as an audible frequency range.

In some embodiments, the reception of signal 48 and the transmission of signal 50 may be carried out using separate coils 60 and 68, respectively. In alternative embodiments, signals 48 and 50 may be both received and transmitted via a single coil, using techniques such as load modulation.

Figure 4:
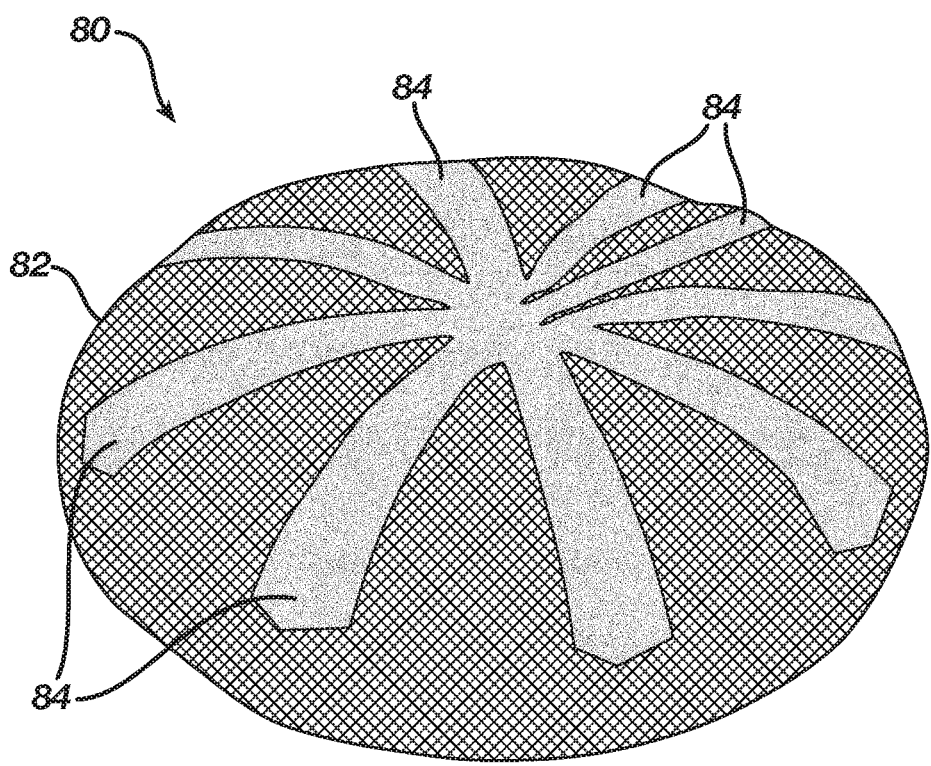
FIG. 4 is a schematic, pictorial illustration of a breast implant, in accordance with an alternative embodiment of the present invention.

FIG. 4 is a schematic, pictorial illustration of a breast implant 80, in accordance with an alternative embodiment of the present invention. Implant 80 may replace, for example, implant 20 of FIG. 2 above. In this embodiment, implant 80 comprises a shell 82, which is configured to encapsulate gel 26 (shown in FIG. 2 above).

Implant 80 further comprises an electrode 84, which may replace, for example, electrode 36 of FIG. 2 above. In some embodiments, electrode 84 may extend over the external circumference of shell 82 so as to cover a large portion of shall 82. In an embodiment, electrode 84 comprises multiple stripes wrapping the shell. In case of a rupture in shell 82, the carbon nanotubes will typically increase the gel conductivity toward the extension of electrode 84 (e.g., one of the stripes) that is closest to the rupture location. The electrode configuration of FIG. 4 thus provides a high sensitivity for detecting the rupture in shell 82.

Although the embodiments described herein mainly address breast implants, the methods and systems described herein can also be used in other applications, such as implants in any other soft tissue in a human body.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

What is claimed is:

1. An implant, comprising:
    a hollow biocompatible shell, which is configured to be implanted in an organ of a patient;
    a first electrode disposed inside the shell;
    a second electrode having at least one surface disposed outside the shell;
    filling material comprising a gel and carbon nanotubes, which fills the shell, and wherein the carbon nanotubes are randomly oriented in the gel when the shell is not ruptured, and in response to a rupture occurring in the shell, some of the gel leaks through the rupture, and the carbon nanotubes change orientation and align toward the rupture, and thus cause a change in electrical conductivity of the filling material between the first electrode and the rupture; and
    circuitry, which is electrically connected to the first and second electrodes and is configured to detect the rupture by sensing the change in the electrical conductivity of the filling material, and to produce an output indicative of the detected rupture.

2. The implant according to claim 1, wherein the filling material comprises silicone gel in which the carbon nanotubes are doped.

3. The implant according to claim 1, wherein the second electrode is electrically insulated from the filling material and electrically connected to a tissue of the organ surrounding the shell.

4. The implant according to claim 1, wherein the circuitry is configured to issue an alert indicative of the rupture to a device external to the patient body.

5. The implant according to claim 1, wherein the circuitry is configured to wirelessly receive electrical power from a device external to the patient body.

6. The implant according to claim 1, and comprising a power source having first and second terminals that are electrically connected to the first and second electrodes, respectively, wherein, in response to the rupture, the power source is configured to drive electrical current via the first and second electrodes and via tissue of the organ surrounding the shell.

7. The implant according to claim 6, wherein the power source is disposed inside the shell.

8. The implant according to claim 6, wherein the circuitry is configured to charge the power source wirelessly from a device external to the patient body.

9. The implant according to claim 6, wherein the power source is configured to supply power to the circuitry.

10. The implant according to claim 1, wherein the shell is configured to electrically insulate the filling material from the organ.

11. The implant according to claim 1, wherein the circuitry is configured to generate an internal operating power wirelessly from a field induced by a device external to the patient body.

12. A system, comprising:
    an implant, comprising:
        a hollow biocompatible shell, which is configured to be implanted in an organ of a patient;
        a first electrode disposed inside the shell;
        a second electrode having at least one surface disposed outside the shell;
    filling material comprising a gel and carbon nanotubes, which fills the shell, and wherein the carbon nanotubes are randomly oriented in the gel when the shell is not ruptured, and in response to a rupture occurring in the shell, some of the gel leaks through the rupture, and the carbon nanotubes change orientation and align toward the rupture, and thus cause a change in electrical conductivity of the filling material between the first electrode and the rupture; and
        circuitry, which is electrically connected to the first and second electrodes and is configured to detect the rupture by sensing the change in the electrical conductivity of the filing material, and to produce an output indicative of the detected rupture; and
        an external device, which is configured to receive the output from the implant and to issue an alert indicative of the detected rupture.

13. The system according to claim 12, wherein the external device is configured to wirelessly induce electrical power to the circuitry.

14. The system according to claim 13, wherein the circuitry is configured to generate an internal operating power wirelessly from a field induced by a device external to the patient body.

* * * * *